United States Patent [19]
Jenkins

[11] Patent Number: 5,109,859
[45] Date of Patent: May 5, 1992

[54] ULTRASOUND GUIDED LASER ANGIOPLASTY

[75] Inventor: Ronald D. Jenkins, Salt Lake City, Utah

[73] Assignee: Beth Israel Hospital Association, Boston, Mass.

[21] Appl. No.: 416,920

[22] Filed: Oct. 4, 1989

[51] Int. Cl.$^5$ ............................................... A61B 8/12
[52] U.S. Cl. ............................ 128/662.03; 128/662.06
[58] Field of Search .................. 128/660.03, 662.06; 600/7

[56] References Cited

U.S. PATENT DOCUMENTS

| | | | |
|---|---|---|---|
| 4,299,266 | 11/1981 | Banka | 128/657 X |
| 4,512,762 | 4/1985 | Spears | 604/21 |
| 4,576,177 | 3/1986 | Webster, Jr. | 128/660.03 |
| 4,641,912 | 2/1987 | Goldenberg | 350/96.10 |
| 4,770,653 | 9/1988 | Shturman | 604/21 |
| 4,799,754 | 1/1989 | Goldenberg | 350/96.18 |
| 4,821,731 | 4/1989 | Martinelli et al. | 128/660.03 X |
| 4,841,977 | 6/1989 | Griffith et al. | 128/660.03 |
| 4,887,605 | 12/1989 | Angelsen et al. | 128/660.03 |
| 4,911,170 | 3/1990 | Thomas, III et al. | 128/660.03 X |
| 4,917,097 | 4/1990 | Proudian, Deceased et al. | 128/662.06 |

Primary Examiner—Francis Jaworski
Attorney, Agent, or Firm—Lorusso & Loud

[57] ABSTRACT

A laser ablation catheter system guided by ultrasound sonography particularly useful for removing atherosclerotic plaque from coronary arteries of patients with heart disease and it method of use are detailed. Ultrasound is employed at the tip of the catheter to determine where the plaque is with reference to the arterial wall. After a sonographic image is made, an ablative laser element is aimed at the plaque to ablatively remove the plaque under computer guidance. In one embodiment, the laser is able to fire in a forward direction after first determining the laser's path to be intralumnal in order to create or recanalize a central channel. In another embodiment, the laser is able to fire circumferentially at the arterial wall guided as to depth and direction by the ultrasound computer interface. Both functions may be provided in one laser angioplasty catheter system. The system also includes manual and computer safety overrides. A proximal occlusion balloon normally will be used to provide stabilization of the catheter and a blood-free environment.

22 Claims, 4 Drawing Sheets

ULTRASOUND GUIDED LASER ANGIOPLASTY

BACKGROUND OF THE INVENTION

This invention relates to medical devices useful for performing laser angioplasty, a specific type of laser surgery designed for the treatment of atherosclerosis and the like.

Atherosclerosis is a disease that causes the thickening and the hardening of the artery walls. It is characterized by lesions of raised atherosclerotic plaque which form within arterial lumens and occlude them partially or wholly. Coronary atherosclerosis tends to increase progressively in humans with age, and is a leading cause of death in the United States. The treatment of atherosclerosis typically includes drug therapy, surgery and/or percutaneous transluminal coronary angioplasty (PTCA).

Progress in interventional cardiovascular techniques has led to increasing reliance on non-surgical coronary and peripheral revascularization such as balloon angioplasty. In keeping with that trend, a complex array of new technologies has been developed that seek to improve on the results of balloon angioplasty. While balloon angioplasty has been a great advancement in treating selected patients with coronary and peripheral vascular disease, it has the possible undesirable effects of causing severe dissection, abrupt closure, and restenosis, such that the chronic result may be worse than the pre-treatment lesion. Moreover, even after ten years of improvements in technique and catheter design, these complications and the degree of their incidence have not changed significantly, albeit, more complex patients are being treated. Indeed, models of experimental atherosclerosis have taught us that endothelial denudation, as produced by balloon abrasion, initiates the proliferative intimal response, allows lipid deposition, and accelerates the atherosclerotic process.

Some of the newer technologies in clinical trials seek to improve the luminal geometry of stenotic lesions aiming at less traumatic restructuring by intravascular stenting, plaque removal by atherectomy or sealing of intimal dissections and decreasing elastic recoil by laser balloon angioplasty. Stents, however, are subject to foreign body reaction and require initial balloon dilation with resultant endothelial injury. The popular atherectomy devices cause mechanical trauma as well as balloon injury from the apposition balloon, and laser balloon angioplasty results in both thermal and balloon injury. While all these procedures have potential clinical applications as adjuncts to balloon angioplasty in the next several years, there is clearly a need for a non-traumatic technique of lesion ablation to carry us into the next era of effective and precise endovascular surgery.

To date the most promising technique suitable for precise tissue removal is that of laser angioplasty. Clinical systems currently in use are primitive at best, particularly those employing conventional lasers for bare fiber or "hot tip" laser angioplasty resulting in largely undirected thermal destruction. Continuous wave conventional lasers, such as the Nd:YAG laser emitting radiation in the near infrared region (1064 nm) and argon lasers emitting light in the visible spectrum, have little utility for efficient tissue removal. At these wavelengths, tissue absorption is diminished resulting in a thermal rather than an ablative process. Part of this problem is due to the absorption spectrum of water, the major constituent of vascular tissue. In contradistinction, peaks of the absorption spectrum in the ultraviolet region around 300 nm, and in infrared region such as at 2900 nm, suggest that lasers such as the XeCl excimer and the erbium YAG lasers, respectively, may be excellent plaque ablators. In fact, clinical data support this finding, with evidence of precise tissue ablation with either laser. The other laser characteristic affecting the degree of the thermal versus the ablative response is the mode of laser delivery, either continuous wave or pulsed. While continuous wave lasers normally lead to deep thermal penetration with possible charring and shallow craters, control of pulse duration and repetition rates can maximize the ablative properties of pulsed lasers as well as positively affect the particle size of ejected tissue. In fact, even pulse lasers can achieve impressive tissue ablation with minimal thermal effects.

Two main technical problems have stood in the way of effective utilization of these lasers clinically. The first is the difficulty of transmitting high power pulsed lasers in conventional fiberoptics. Recently, however, the excimer laser has been transmitted down a 200 micron fiberoptic using an expanded pulse technique, and prototype fiberoptics show considerable promise for transmitting erbium YAG laser radiation. It is therefore likely that fiberoptic capability will not be the limiting factor for development of a successful laser angioplasty system using these lasers. The second and more substantial problem that prevents clinical utility of an ablative laser is that of providing safe, reliable and precise laser guidance to change an intravascular weapon to a precision instrument. To date most laser ablative systems employ a forward firing laser beam with or without a metal cap and constructed with or without a lens systems to convert laser energy into purely thermal energy. These types of systems are all capable of opening channels to various degrees, with some utility in the case of total occlusions, by allowing passage of a guide wire for subsequent balloon angioplasty. However, none of these systems can achieve a normal luminal diameter as sole therapy. Angiographic guidance of these laser catheters has not been completely successful and is fraught with the hazard of vascular perforation, particularly in tortuous segments. While the peripheral arterial vasculature is large, straight, and relatively forgiving in the case of perforation, the coronary circulation shares none of these characteristics, and perforation is therefore intolerable. Alterations in tip design, while somewhat helpful in improving trackability, cannot lead to precise or reliable guidance. One known guidance method is the use of a proximal centering balloon for a laser angioplasty system. While this device has some utility in straight arteries for crossing shorter occlusions wherein the arterial segment proximal to the occlusion is free of disease and therefore results in appropriate centering, these conditions are infrequently met, and also require the use of balloon angioplasty with its known limitations.

A second known system for use in ablative laser angioplasty employs tracking of the laser catheter over a conventional guidewire. While the use of guidewire offers the only reasonably safe method of using an ablating laser at the present time, the inability to determine precise depths of laser penetration continues to result in ineffective luminal improvement and often requires subsequent balloon angioplasty.

Interest in creating a laser ablative system that distinguishes between normal and atherosclerotic tissue has led to the development of the concept of a spectroscopic guidance laser angioplasty system. This so-called "smart" laser is based on the premise that the induced fluorescence of atherosclerotic plaque provides an altered spectroscopic pattern, which, in turn, signals a computer generated algorithm to allow further laser pulses until a normal pattern is recognized. This system, however, requires direct apposition of a fiberoptic with the plaque, making intravascular application unfeasible without further guidance to direct the laser to circumferential lesions. In practice, however, the difference between normal and abnormal tissue is not always evident fron the spectroscopic pattern and atheroslerotic tissue can be full thickness, obviously allowing the potential for perforation.

Intraluminal sonography, recently miniaturized for percutaneous intravascular use, is one tool capable of circumferential imaging. Current technology allows imaging catheters as small as 0.8 mm with either phased array or rotating mechanical transducers, and either central channel or monorail systems for guidewire use. Catheters are now able to image vessels to 2 mm diameter and will likely be miniaturized further, making this a feasible imaging modality for coronary use.

Intraluminal sonography demonstrates distinct layers of the arterial wall. The intima and adventitia are echogenic, unlike the healthy media which is hypoechoic. Atherosclerotic plaques are echogenic and become hyperechoic when calcified, at times to the point of causing shadowing behind the structure. Vascular imaging has been shown to be extremely accurate in camparison to histologic sections of in-vitro human carotid and iliac vessels. Intraluminal sonography has been studied in dogs and pigs to image iliac, cerebral, mesenteric and coronary arteries. It has been documented to clearly define plaque removal by atherectomy as well. Therefore, as other imaging modalities fail to give as precise structural detail, intraluminal ultrasound appears to be a superior technology for guiding intravascular procedures such as laser angioplasty.

SUMMARY OF THE INVENTION

The present invention is a laser ablation catheter system and method for removal of atherosclerotic plaque. The laser ablation device incorporates a phased array ultrasound transducer at the distal end of a catheter which contains a central channel for guidance and manipulation. A low pressure concentric balloon similar to that used in pulmonary artery floatation catheters, of greater length and width and capable of expanding to a width of about half a centimeter, is placed near the distal tip of the catheter. It provides brief artery occlusion both for catheter stabilization and blood displacement for more effective laser penetration. Blood disbursement is performed by flushing warmed (37° C.), heparinized physiologic saline through a central channel during lasing. An automatic laser shut-off device is employed in the case of fiberoptic failure or fracture so that laser energy is not released in an inappropriate place such as along the shaft of the catheter. It is envisioned that the laser catheter of the present invention can fire laser energy both forward of and lateral to the distal end of the catheter. The forward firing laser catheter is used to remove either partial or whole occlusions from the center of the lumen while the lateral firing laser catheter is used to remove plaque from the artery wall. These functions of the laser catheter could be provided by one laser catheter or by two separate catheters.

The method for removing atherosclerotic plaque comprises providing an ultrasound guided laser ablation catheter system, positioning the catheter, and using it to provide a directed pulse of laser energy to remove the plaque.

Accordingly, it is an object of the present invention to provide a system for delivering forward directed laser energy using an ultrasound guidance system for vascular recanalization.

Another object of the present invention is to provide a lateral firing pulsed laser guided by intravascular sonography (ultrasound).

A further object of the present invention is to deliver pulsed laser energy both in a forward direction to gain access through total or subtotal occlusions and in lateral directions circumferentially, guided by an imaging system to direct the depth of ablation.

Yet another object of the present invention is to transform ultrasound generated vascular images into information that will direct laser usage and distribution, using algorithms which will generate and send signals to the laser device based on continuous images which provide the delineation of the luminal surface, the internal elastic lamina and the adventitia and which will be sampled on-line by a computer processor to obtain the circumferential measurements of vessel thickness, plaque thickness, and distance of the catheter exterior to the luminal surface.

Other objects and details of the present invention will become apparent from the detailed descriptions which follows, taken in conjuction with the accompanying drawings, in which like reference numbers refer to like elements in the various figure.

DESCRIPTION OF THE PREFERRED EMBODIMENTS

Figure 1A:
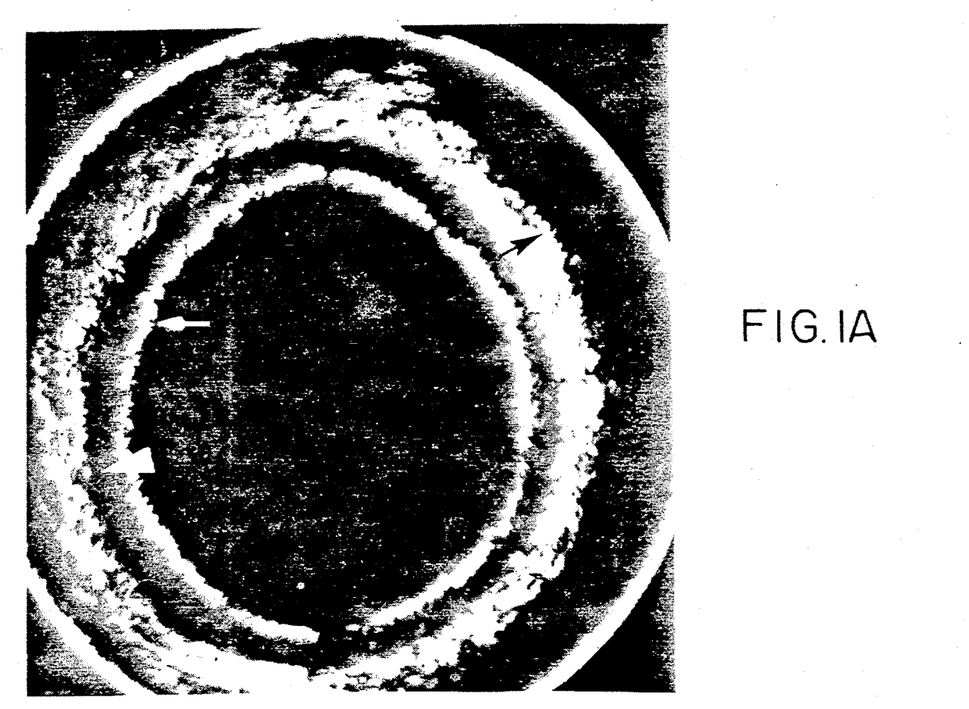
FIG. 1A shows a transaxial image of a normal artery using intraluminal sonography.
Figure 1B:
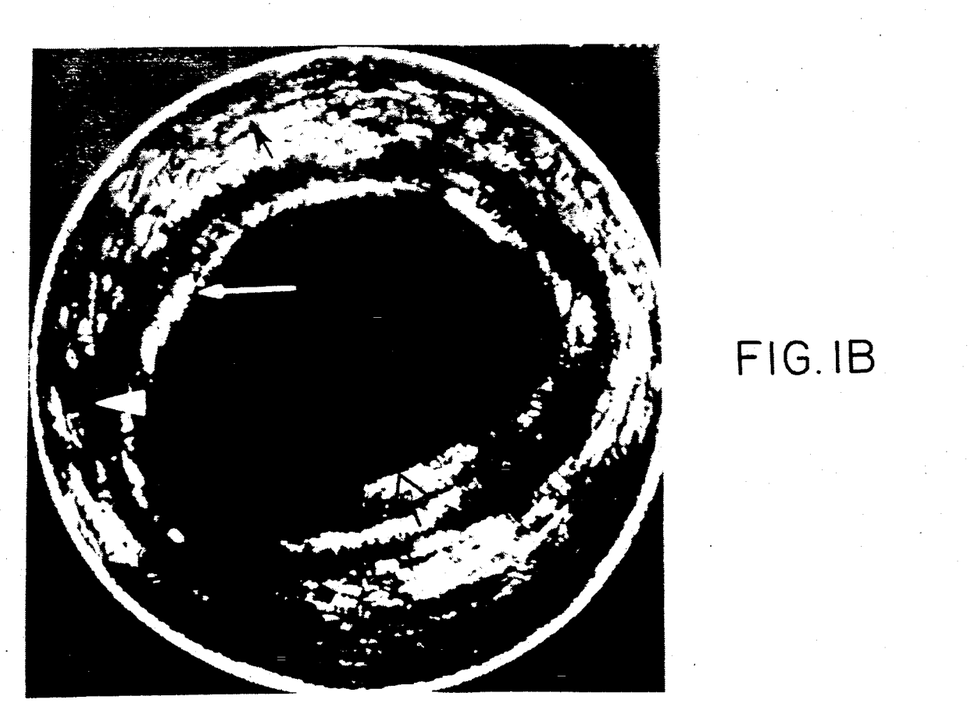
FIG. 1B shows a transaxial image of an atherosclerotic artery.

Referring to FIGS. 1A and B intraluminal sonography demonstrates distinct layers of the arterial wall. Vascular imaging has been shown to be extremely accurate in comparison to histological sections of in-vitro human carotid and iliac vessels. As shown in FIG. 1A, normal artery demonstrates an echogenic intima (white arrows) and adventitia (black arrows), while the media is hypoechoic (white arrowheads). In FIG. 1B, atherosclerotic artery shows a thickened echogenic neointima (open black arrow), plaque (area between neointima and media), and adventitia (black arrow) typical of an atherosclerotic vessel. Intraluminal sonography is thus employed in the catheter of the present invention to provide vascular structural delineation from which computer derived vascular measurements can be used to guide the intravascular laser angioplasty.

The first embodiment of the present invention is to be used for opening total or subtotal occlusions to allow passage of conventional or other interventional hardware. This catheter, shown in FIGS. 2A and 2B, has a 3.5 French (Fr.) external diameter and produces vascular images circumferentially with a 20 MHz phased array transducer 10. A central lumen phased array imaging catheter with similar characteristics although without an occlusion balloon or laser capability is currently available in a 5.5 Fr. size from EndoSonics Corp., Rancho Cordova, Calif. A 3-4 Fr. imaging catheter is anticipated from the same manufacturer within the year.

Figures 2A, 2B:
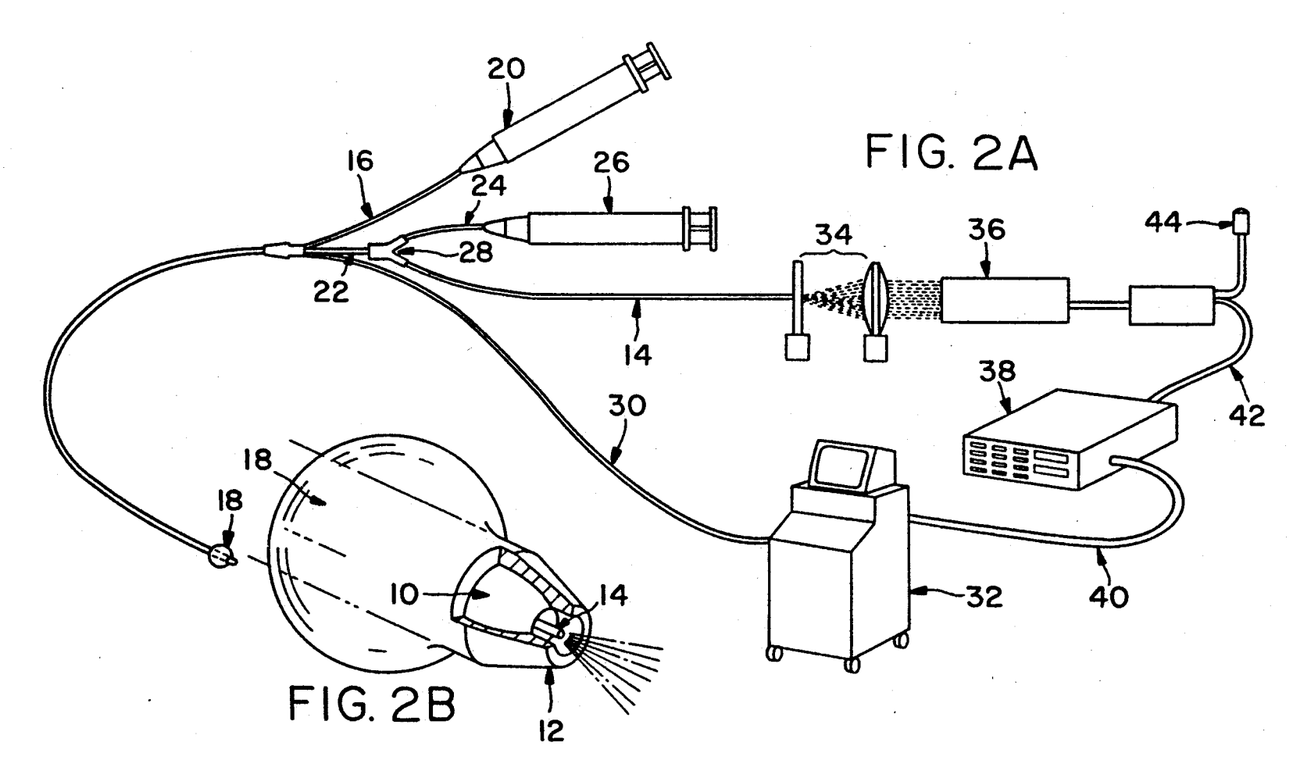
FIG. 2A is a schematic diagram, of a sonography guided pulsed laser recanalization system (catheter plus hardware) of the present invention.
FIG. 2B shows an enlarged view of an occlusion balloon shown in FIG. 2A.

The described catheter will produce images of vascular tissue acquired in a plane that is 30° forward of the tip 12 of the catheter to insure a central location or laser direction up to 2 mm beyond the catheter tip 12 (i.e. through the course of the intended laser beam) as insurance against vascular perforation. A central 0.014 inch conventional guidewire (not shown) may be exchanged for a 200 micron laser fiberoptic 14 designed to terminate in the tip 12 of the catheter, 1 mm recessed to protect against fiber damage. The fiberoptic 14 emits pulsed laser radiation from the lens (not shown) at the tip of the fiberoptic 14 with a dispersion angle of 30° such that a 1.3 mm diameter, 2 mm deep crater is produced with each pulsetrain, permitting passage of the catheter into the crater.

Proximal catheter ports include an occlusion balloon port 16 for inflation of the centering balloon 18 by the inflation syringe 20, a central channel 22 300 microns in diameter for either the guidewire or the fiberoptic 14 with a side port 16 for a flushing syringe 26 connected via a Tuohy-Borst adapter, and a sonography port 30 for connection to the ultrasound monitor 32. A standard coupling device 34 is employed for coupling the fiberoptic 14 to the pulsed laser 36. Also shown is the central processing unit 38 connected to the ultrasound console 32 via the monitor output 40 and to the laser 36 via the laser interface 42 which can interrupt signals from the firing mechanism 44.

In clinical use, this catheter is introduced percutaneously through a standard 8 Fr. guiding catheter over a 0.014 inch guidewire into the coronary artery to be treated using standard catheterization techniques. Once the catheter abuts a total or subtotal occlusion, the guidewire is exchanged for the 200 micron laser fiberoptic 14 and connected to the pulsed laser 36 after appropriate safety and functional testing. The catheter is positioned centrally using ultrasound guidance considering the distance of the catheter to the adventitia circumferentially during inflation of the low pressure occlusion balloon 18. Infusion of warm physiologic saline at a rate of 0.25 to 0.5 cc/sec through the side port 24 of the central channel 22 insures clearing of the area during the anticipated 3 to 5 second pulsetrain of laser energy. The operator initiates each pulsetrain via the firing mechanism 44 only after verifying correct central catheter position. If an eccentric location is chosen (i.e. within 600 microns of the advantitia on any side) laser delivery is prevented by output from the ultrasound monitor 32 through the interface 40 to the central processing unit 38 which triggers automatic laser shutdown via the laser interface 42. After each laser dose, contrast is injected through the guiding catheter to check for recanalization. Assuming only crater formation without recanalization after the first laser burst, the balloon 18 is let down and the catheter advanced into the crater. The balloon 18 is then reinflated, the position checked by ultrasound using the monitor 32, and if appropriate, a further laser burst is initiated during central channel flushing. This format is continued (positioning, lasing, advancing) At 1-2 mm increments until the catheter is through the occlusion as judged by sonography and contrast angiography. At that point, the laser fiberoptic 14 is exchanged for the guidewire in anticipation of further intervention such as balloon angioplasty or use of the circumferential laser ablating catheter which is described below.

While this technique is feasible and safe for the coronary circulation, it is impractical for long total occlusions that might occur in the peripheral circulation where it may be appropriate to use a continuous imaging and lasing technique, advancing the catheter with the occlusion balloon deflated, and stopping only when the catheter becomes unduly eccentric by an automatic shut-off via the laser interface 42, or when the catheter has traversed the occlusion, as judged by sonography and continuous contrast injection through the central channel side port 24.

Figures 3A, 3B:
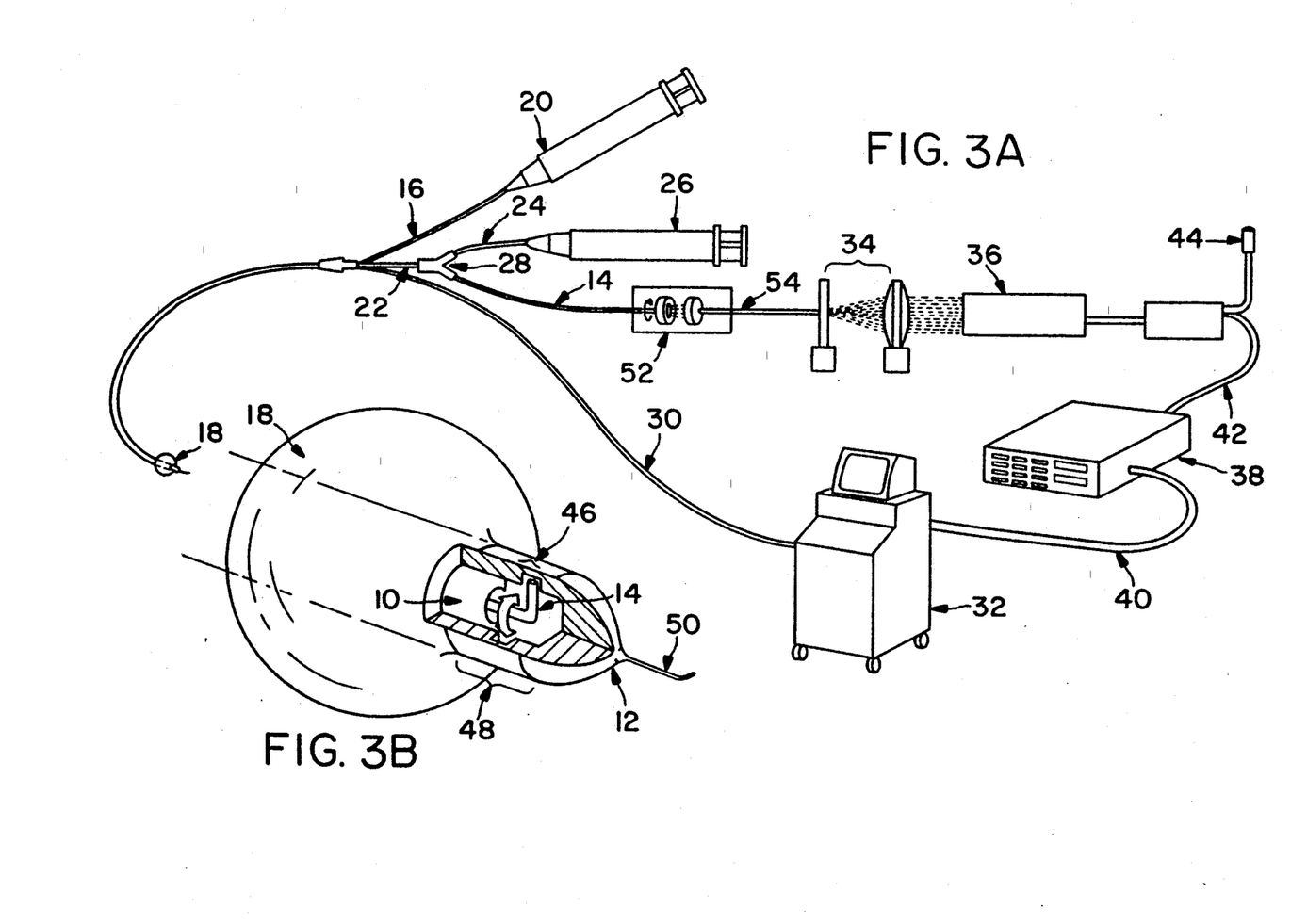
FIG. 3A is a schematic diagram, of a sonography guided lateral firing pulsed laser plaque ablation system (catheter plus hardware) of the present inventon.
FIG. 3B shows an enlarged view of an occlusion balloon shown in FIG. 3A.

The second embodiment described is a lateral firing sonography guided pulsed laser ablation catheter, shown in FIGS. 3A and 3B This 4 Fr. catheter includes a distal 20 MHz phased array transducer 10 with a 400 micron diameter central lumen 22. Within the central lumen 22 is a 200 micron fiberoptic 14 which bends acutely at the distal end of the transducer 10, pointing laterally into a sleeve (not shown) and freely rotating 360° about the catheter within a circumferential groove or "track" 46. The track 46 is defined in a silica or plastic lens cylinder 48 which encapsulates the fiberoptic 14 as it turns, providing unimpeded exit of the laser energy, yet protection from trauma to the fiber. The most distal tip 12 has a polyethylene cover 8 and terminates with a variable length (1-3 cm) guidewire 50, akin to the USCI "Probe" angioplasty catheter (USCI, Division of C. R. Bard, Inc., 1200 Technology Park Drive, Billerica, MA). Perforations (not shown) within the polyethylene cover allow circumferential flushing during lasing.

Proximal catheter ports include a balloon occlusion port 16, a sonography port 30, and a central channel 22 containing the fiberoptic 14 coursing through a Tuohy-Borst adapter 28 for flushing through the side port 24. The fiberoptic 14 terminates proximally in a rotation module 52 that allows rotation of the proximal catheter fiber terminus in relation to the connecting jumper fiber 54 interfacing with the laser through a standard coupling device 34 while maintaining axial alignment with the connecting segment 54. The rotation module 52 also provides for constant revolution of the fiberoptic 14 initiated at its proximal terminus.

This catheter is introduced percutaneously through a standard 8 Fr. guiding catheter. To negotiate tortuous proximal anatomy, a somewhat smaller subselective guiding sheath may be used (such as the USCI Probe catheter). The catheter is advanced to the lesion in question via angiographic guidance. Ideally, it is advanced distal to the lesion and pulled back through it during lasing, although advancing through the lesion antegrade is also acceptable. Sonographic imaging provides circumferential wall thickness in the same plane as the laser fiberoptic path, specifically providing thickness data in thirty-six segments corresponding to "stops" of the laser fiber, each subtending 10° of the 360° arc. The track sleeve, while revolving at several Hz, provides an ultrasound signal that serves as a reference for correlation of data in relation to the fiberoptic position.

In use, the proximal occlusion balloon 18 is inflated by operation of an inflation syringe 20, and flushing through the central channel side port 24 is commenced by operation of a flush syringe 26. Ultrasound imaging and fiberoptic rotation is then initiated. Once the computer 38 communicating with the laser 36 via the laser interface 42 and interfaced to the ultrasound monitor 32 via the ultrasound output 40 is manually activated by depressing the firing mechanism 44, the laser 36 begins firing pulses sequentially at thirty-six stops around the catheter at several Hz as directed by a computer algorithm. Table I shows a sample algorithm. Interrogation at each 10° sector provides wall thickness data on each revolution of the fiberoptic.

TABLE I

Algorithm for Sonography Guided Laser Angioplasty
(Laser *Fire* command set for wall thickness > 500 Microns)

| Sectors (10 degrees each) | | Wall Thickness (microns) | Command to Laser |
|---|---|---|---|
| 1 | 0°-9° | 400 | No Fire |
| 2 | 10°-19° | 400 | No Fire |
| 3 | 20°-29° | 400 | No Fire |
| 4 | 30°-39° | 400 | No Fire |
| 5 | 40°-49° | 400 | No Fire |
| 6 | 50°-59° | 500 | No Fire |
| 7 | 60°-69° | 510 | *Fire* |
| 8 | 70°-79° | 540 | *Fire* |
| 9 | 80°-89° | 650 | *Fire* |
| 10 | 90°-99° | 650 | *Fire* |
| 11 | 100°-109° | 650 | *Fire* |
| 12 | 110°-119° | 650 | *Fire* |
| 13 | 120°-129° | 650 | *Fire* |
| 14 | 130°-139° | 650 | *Fire* |
| 15 | 140°-149° | 650 | *Fire* |
| 16 | 150°-159° | 650 | *Fire* |
| 17 | 160°-169° | 500 | No Fire |
| 18 | 170°-179° | 400 | No Fire |
| 19 | 180°-189° | 400 | No Fire |
| 20 | 190°-199° | 400 | No Fire |
| 21 | 200°-209° | 400 | No Fire |
| 22 | 210°-219° | 400 | No Fire |
| 23 | 220°-229° | 400 | No Fire |
| 24 | 230°-239° | 400 | No Fire |
| 25 | 240°-249° | 400 | No Fire |
| 26 | 250°-259° | 400 | No Fire |
| 27 | 260°-269° | 400 | No Fire |
| 28 | 270°-279° | 400 | No Fire |
| 29 | 280°-289° | 400 | No Fire |
| 30 | 290°-299° | 400 | No Fire |
| 31 | 300°-309° | 400 | No Fire |
| 32 | 310°-319° | 400 | No Fire |
| 33 | 320°-329° | 400 | No Fire |
| 34 | 330°-339° | 400 | No Fire |
| 35 | 340°-349° | 400 | No Fire |
| 36 | 350°-359° | 400 | No Fire |

Any detected thickness in excess of a determined "normal" thickness, arbitrarily 500 microns in the example, triggers a response to the laser 36 and generates a fire signal when the fiberoptic 14 reaches that particular 10° sector or stop. In the case shown in Table I, a fire signal is generated only between the stops at 60° and 150° inclusive. In turn, when the predetermined thickness is achieved or is already present in certain segments, the signal changes to "no fire" and a laser pulse is not emitted for those segments or stops. In general, interrogation occurs in segments subtending arcs immediately prior to the path of the fiberoptic 14 so that the decision to fire or not is instantaneous upon the fiberoptic 14 reaching a sector. Adjusting the speed of the fiberoptic revolution and pulse width insures that the full 10° arc is completely exposed to the laser energy, although a small amount of segment overlap may be advantageous. The sequential lasing continues until no further lesion is recognized in any of the thirty-six 10° segments. At this point, the catheter is withdrawn or advanced until a "fire" signal is again achieved, and the process continues until successful lesion ablation is achieved. Periodic contrast angiography can be used to verify ablation, which is also documented by the sonographic luminal dimensions.

In a preferred embodiment, the lateral firing laser is provided with a safety feature which consists of a firing mechanism 44 that must be depressed continuously by the operator so that the "fire" or "no fire" singals are received by the laser 36 and pulses generated as appropriate. That is, when the mechanism 44 is not depressed, signals are generated but not sent to the laser 36 via the laser input interface 42. This system allows a double check that signals are appropriately based on wall thickness data for the thirty-six segments, as displayed on the monitor 32 with the sonographic image. If the operator desires to override the computer algorithm commands, releasing the mechanism 44 causes immediate cessation of lasing.

Figures 4A, 4B:
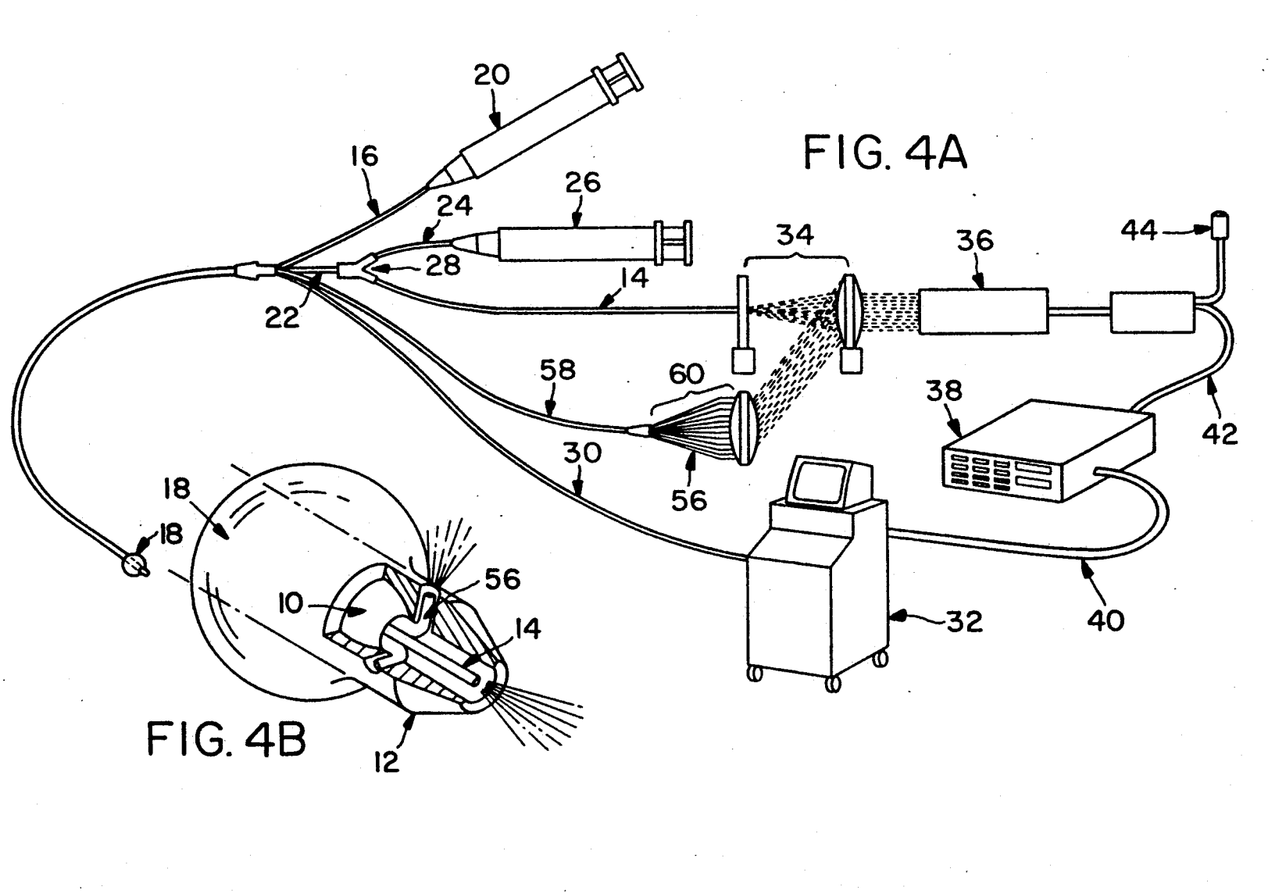
FIG. 4A is a schematic diagram, of a sonography guided recanalization and lateral firing pulsed laser plaque ablation system (catheter plus hardware) of the present invention.
FIG. 4B shows an enlarged view of an occlusion balloon shown in FIG. 4A.

In a third embodiment, a combined recanalization and debulking sonography guided laser ablation catheter is described. Such a catheter is shown in FIGS. 4A and 4B. The basic design of such a catheter is similar to the first described forward firing catheter wherein the laser fiberoptic 14 is exchanged for a guidewire through the central channel coursing through the 20 MHz phased array ultrasound transducer 10. In addition, however, it contains from twelve to thirty-six optical fibers 56 approximately 50 microns in core diameter (only two are shown in the expanded diagram for clarity), each emerging laterally just proximal to the tip 12 of the catheter and just distal to the imaging transducer 10 and again pointing to the same plane of imaging. Each fiberoptic 56 subtends a 10° to 30° arc with some degree of overlap, perhaps 5° on either side of each segment to insure a more homogeneous ablation. Each fiberoptic 56 is independently pulsed in a "Gatling gun" arrangement.

Proximal catheter ports include a sonography port 30, an occlusion balloon port 16, a central guidewire fiberoptic channel 22 with a side port 24 for flushing, and a twelve to thirty-six fiberoptic bundle 58 that interfaces with the laser 36 via a linear array of mirrors 60 that can be rapidly turned to allow laser energy to sequentially track down each fiberoptic 56 separately.

This catheter can, therefore, be used in a fashion as either of the previously described catheters. The central laser fiberoptic 14 is placed only when needed for recanalization. The new channel, in turn, allows passage of the catheter into the lesion which is ablated subsequently by lateral laser angioplasty. Again, wall thickness is interrogated at each segment before anticipated lasing, so that the signal occurs on time in a sequential fashion, firing laser pulses around the catheter at several Hz.

As can be seen from the descriptions of the catheters, balloon occlusion is useful for improving visualization and for removing blood from the path of laser disbursement. However, as improvements are made in the ultrasonic transducers, motion artifact will be reduced making balloon occlusion less necessary. In addition, some lasers such as the excimer, are able to penetrate blood to a few millimeters in depth with undiminished capability of tissue ablation. Therefore, balloon occlusion may not always be a necessary component of the system. In any event, balloon occlusion times are expected to be short, i.e. less than forty seconds, thus limiting ischemia to an acceptable range. Debris created by laser ablation is a particularly important problem. Certainly any technique that creates a significant number of particles with diameters greater than 7 microns will be fraught with embolization into distal capillary beds leading to sluggish antegrade flow and profound ischemia. The size of the particular debris is affected by power and pulse characteristics of the laser. Furthermore, plaque debris, particularly from a lased thrombus, can be highly thrombogenic. It is therefore quite important that a shallow penetrating, highly vaporizing laser be used for this system particularly when contemplating multilesion laser angioplasty. Lasers such as the excimer holmium and erbium YAG are pulsed lasers available from many laser manufacturers, such as Quontronix Corp. (Smithtown, NY), that share these features.

Finally, although some studies suggest that surface thrombogenicity may be reduced after plaque ablation, the loss of endothelium and exposure of subendothelial collagen can be expected to accelerate platelet deposition with risk of thrombus formation which may initiate a proliferative response that could lead to restenosis. In that light, pharmacologic therapy aimed at reducing platelet deposition during the period of endothelial regeneration is an important adjunctive measure. While liberal use of dextran in addition to aspirin and heparin appears to be helpful in reducing platelet deposition after procedures such as intercoronary stent placement, newer agents undergoing clinical study may offer further benefit during the period of endothelial regeneration.

While the foregoing invention has been described with reference to its preferred embodiments, it should not be limited to such embodiments since various alterations and modifications will occur to those skilled in the art. For example, numerous types of ablative lasers can be used in the system described. These and other alterations and modifications are intended to fall within the scope of the appended claims.

What is claim is:

1. A method for removing atherosclerotic plaque from artery walls comprising:
   (a) providing a source of laser energy;
   (b) inserting a laser angioplasty catheter into an artery which contains atherosclerotic plaque, said laser angioplasty catheter having a fiberoptic waveguide along a long axis of said catheter and an ultrasonic transducer, said fiberoptic waveguide having a proximal end and a distal end with said fiberoptic waveguide having a bend at a right angle to the length of the catheter just before said distal end so that said fiberoptic waveguide can be rotated such that said distal end can trace out a circular path in a plane perpendicular to the length of the catheter, said fiberoptic waveguide being for receiving the laser energy at the proximal end and conducting the laser energy to the distal end, said ultrasonic transducer being capable of providing an intraluminal image to an ultrasound monitor;
   (c) providing a circumferential groove in said laser angioplasty catheter for the containment of said right angle bend in said fiberoptic waveguide,
   (d) covering said right angle bend of said fiberoptic waveguide with a track sleeve that serves as an Ultrasonic reference for said ultrasonic transducer;
   (e) inflating an occlusion balloon proximal to said ultrasonic transducer for stabilizing said transducer and the image produced thereby and for temporary occlusion of blood flow;
   (f) flushing the area in the artery containing the atherosclerotic plaque with a warm physiologic saline through an opening in said laser angioplasty catheter;
   (g) taking an intraluminal image of the artery by use of said ultrasound transducer to determine the position and thickness of the atherosclerotic plaque within the artery in relation to said ultrasonic reference;
   (h) using said data regarding position and thickness of the atherosclerotic plaque within the artery to rotate said distal end of said fiberoptic waveguide so that said distal end is adjacent to vessel wall atherosclerotic plaque; and
   (i) initiating a pluse of laser energy.

2. The method according to claim 1 wherein said artery is a coronary artery.

3. The method according to claim 1 further comprising:
   repeating steps (g)–(i) until all the atherosclerotic plaque is removed to a pre-set vascular thickness.

4. The method of claim 3 further comprising administering pharmacological therapy after the atherosclerotic plaque is removed to a pre-set vascular thickness, in order to reduce platelet deposition during the period of endothelial regeneration following said removal of atherosclerotic plaque.

5. The method of claim 4 wherein said administering step comprises administering therapeutic agents in the period of endothelial regeneration following said removal of atherosclerotic plaque, the therapeutic agents being selected from the group of dextran, aspirin, and heparin.

6. A method for recanalizing a vessel which is partially or wholly occluded by atherosclerotic plaque comprising:
   (a) providing a source of laser energy;
   (b) inserting a laser angioplasty catheter having a proximal and a distal end into an artery which is partially or wholly occluded by atherosclerotic plaque, said angioplasty catheter comprising a fiberoptic waveguide running along the long central axis of said catheter, said fiberoptic waveguide having a proximal and a distal end for receiving the laser energy at the proximal end and conducting the laser energy to the distal end;
   (c) providing an ultrasound transducer at the distal end of said laser angioplasty catheter, said ultrasonic transducer being capable of providing an intraluminal image to an ultrasound monitor for guiding said laser angioplasty catheter;
   (d) inflating an occlusion balloon proximal to said ultrasonic transducer for stabilizing said transducer and the image produced thereby and for temporary occlusion of blood flow;

(e) flushing the area in the artery which is wholly or partially occluded with warm physiologic saline through an opening in said laser angioplasty catheter;

(f) taking an intraluminal image of the artery to determine the distance and direction of the atherosclerotic plaque within the artery, to provide a reference for centering said laser angioplasty catheter within said artery, and to ensure an intraluminal path for the laser energy;

(g) positioning said fiberoptic waveguide within the artery so that the distal end is pointing at atherosclerotic plaque as determined by said ultrasonic transducer; and (h) initiating a pulse of laser energy.

7. The method according to claim 6 wherein said artery is a coronary artery.

8. The method according to claim 7 further comprising:
repeating steps (d)–(h) until a central channel is recanalized.

9. The method of claim 8 further comprising administering pharmacological therapy after the central channel is recanalized, in order to reduce platelet deposition during the period of endothelial regeneration following said recanalization of the central channel.

10. The method of claim 9 wherein said administering step comprises administering therapeutic agents in the period of endothelial regeneration following said recanalization of the central channel, the therapeutic agents being selected from the group of dextran, aspirin, and heparin.

11. The method according to claim 5 wherein the rotating of the distal end of the fiberoptic waveguide so that said distal end is adjacent to vessel wall atherosclerotic plaque is achieved by providing that said fiberoptic waveguide is continually rotating such that said distal end is tracing out a circular path in a plane perpendicular to the length of said laser angioplasty catheter and said ultrasonic transducer is periodically taking one of a plurality of intraluminal images, said one of a plurality being and intraluminal image of a portion of the vessel wall of said artery, said portion of said vessel wall being located slightly ahead of the then present position of said distal end of said fiberoptic waveguide such that the thickness of the vessel wall is determined just before said distal end of said fiberoptic waveguide arrives at said portion of the vessel wall and if the thickness of said portion of said vessel wall is larger than said pre-set thickness, a pulse of laser energy is initiated when said distal end arrives at said portion of said vessel wall.

12. The method according to claim 11 wherein said initiation of a pulse of laser energy can be prevented by an operator releasing a firing mechanism which must be depressed in order for said pulse of laser energy to be initiated.

13. The method according to claim 12 wherein the energy of said laser pulse is selected to be shallowly penetrating and highly vaporizing such that the particles created by removal of the atherosclerotic plaque are smaller than 7 microns in diameter.

14. The method according to claim 10 wherein the initiation of a pulse of laser energy is automatically inhibited if a determination is made from said intraluminal image that the positioning of said distal end of said fiberoptic waveguide is eccentric and firing of said laser may cause arterial damage.

15. The method according to claim 14 wherein the energy of said laser pulse is selected to be shallowly penetrating and highly vaporizing such that the particles created by removal of the atherosclerotic plaque are smaller than 7 microns in diameter.

16. A method for recanalizing a vessel which is wholly or partially occluded by atherosclerotic plaque and debulking the vessel wall surrounding the remnant of said occlusion comprising:

(a) providing a source of laser energy;

(b) inserting a laser angioplasty catheter having a proximal and distal end into an artery which is wholly or partially occluded by atherosclerotic plaque;

(c) providing a plurality of fiberoptic waveguides with proximal and distal ends for receiving the laser energy at the proximal end and conducting the laser energy to the distal end, said fiberoptic waveguides being disposed within said laser angioplasty catheter, one of said fiberoptic waveguides running along the long central axis of said catheter and terminating just before the distal end of said catheter, the remaining of said plurality of fiberoptic waveguides running parallel to the long central axis of said catheter and having a bend at a right angle to the length of the catheter just before their distal ends such that the distal ends are spaced equidistantly along a first circular path, the plane defined by said first circular path being perpendicular to the long central axis of said catheter;

(d) providing an ultrasound transducer at the distal end of said laser angioplasty catheter, said ultrasonic transducer being capable of providing an intraluminal image to an ultrasound monitor;

(e) inflating an occlusion balloon proximal to said ultrasonic transducer for stabilizing said transducer and the image produced thereby and for temporary occlusion of blood flow;

(f) flushing the area in the artery which is wholly or partially occluded with warm physiologic saline through an opening in said laser angioplasty catheter;

(g) taking an intraluminal image of the artery to determine the distance and direction of the atherosclerotic plaque within the artery to provide a reference for centering said catheter within said artery and to ensure an intraluminal path for the laser energy;

(h) positioning said fiberoptic waveguide running along the central axis of said catheter so that the distal end of said fiberoptic waveguide is pointing at atherosclerotic plaque as determined by said ultrasonic transducer;

(i) initiating a pulse of laser energy;

(j) repeating steps (e)–(i) until a central channel is recanalized that is large enough for passage of the distal end of said catheter;

(k) deflating said occlusion balloon;

(l) taking an intraluminal image of the artery to determined the location of the remnant of the partially or wholly occluding plaque;

(m) advancing said catheter distally until said first circular path is at said remnant of the occluding plaque as determined from said intraluminal image;

(n) inflating an occlusion balloon proximal to said ultrasonic transducer for stabilizing said transducer and the image produced thereby and for the temporary occlusion of blood flow;

(o) flushing the area in the artery containing the plaque with a warm physiologic saline through an opening in said catheter;

(p) providing a laser diverting means for directing said laser sequentially to the proximal end of said fiberoptic waveguides having said right angle bend just before their distal ends such that the laser energy is capable of being transmitted sequentially through the distal ends of said fiberoptic waveguides arranged in said first circular path, thereby defining a second circular path along the vessel wall of said artery made up of a plurality of sections, each section corresponding to one of said fiberoptic waveguides;

(q) taking one of a plurality opf ultrasonic images in the plane of said second circular path, said intraluminal image being of one of said plurality of sections of said second circular path along the vessel wall, said section being located at a point further along said second circular path and adjacent to the section then capable of being irradiated by said laser energy;

(r) determining the thickness of said section of the vessel wall;

(s) initiating a pulse of laser energy when the laser is diverted to the proximal end of the fiberoptic waveguide corresponding to said section of the vessel wall if the thickness is greater than a pre-set thickness, thereby causing irradiation of said section of the vessel wall;

(t) repeating steps (q)-(s) until all of the plurality of sections making up said second circular path have thicknesses below the pre-set thickness.

17. The method according to claim 16, wherein said artery is a coronary artery.

18. The method of claim 17 further comprising administering pharmacological therapy after the atherosclerotic plaque is removed to a pre-set vascular thickness, in order to reduce platelet deposition during the period of endothelial regeneration following said removal of atherosclerotic plaque.

19. The method of claim 18 wherein said administering step comprises administering therapeutic agents in the period of endothelial regeneration following said removal of atherosclerotic plaque, the therapeutic agents being selected from the group of dextran, aspirin, and heparin.

20. The method according to claim 19 wherein said initiation of a pulse of laser energy can be prevented by an operator releasing a firing mechanism which must be depressed in order for said pulse of laser energy to be initiated.

21. The method according to claim 20 wherein the initiation of a pulse of laser energy is automatically inhibited if a determination is made form said intraluminal image that the positioning of said distal end of said fiberoptic waveguide is eccentric and firing of said laser may cause arterial damage.

22. The method according to claim 21 wherein the energy of said laser pulse is selected to be shallowly penetrating and highly vaporizing such that the particles created by removal of the atherosclerotic plaque are smaller than 7 microns in diameter.

* * * * *